(12) United States Patent
Eberhard et al.

(10) Patent No.: US 6,654,622 B1
(45) Date of Patent: Nov. 25, 2003

(54) DEVICE FOR THE COMBINED MEASUREMENT OF THE ARTERIAL OXYGEN SATURATION AND THE TRANSCUTANEOUS $CO_2$ PARTIAL PRESSURE ON AN EAR LOBE

(75) Inventors: Patrick Eberhard, Bottmingen (CH); Jean-Pierre Palma, Pratteln (CH)

(73) Assignee: Linde Medical Sensors AG, Basel (CH)

( * ) Notice: Subject to any disclaimer, the term of this patent is extended or adjusted under 35 U.S.C. 154(b) by 0 days.

(21) Appl. No.: 09/452,218

(22) Filed: Dec. 1, 1999

(30) Foreign Application Priority Data

Nov. 19, 1999 (CA) .............................. 2290083

(51) Int. Cl.[7] .................................. A61B 5/00
(52) U.S. Cl. .................. 600/326; 600/322; 600/353
(58) Field of Search ............... 600/309–311, 322–323, 600/340, 344, 348, 353, 354, 361; 204/412, 403, 415

(56) References Cited

U.S. PATENT DOCUMENTS

| | | | |
|---|---|---|---|
| 4,274,418 A | * 6/1981 | Vesterager et al. ......... 600/354 |
| 4,384,586 A | * 5/1983 | Christiansen ............... 600/361 |
| 4,789,453 A | 12/1988 | Eberhard et al. |
| 4,840,179 A | 6/1989 | Ullrich |
| 4,930,506 A | 6/1990 | Ullrich |
| 5,131,391 A | * 7/1992 | Sakai et al. ................. 600/334 |
| 5,337,744 A | 8/1994 | Branigan |
| 5,348,003 A | * 9/1994 | Caro .......................... 600/310 |
| 5,452,717 A | 9/1995 | Branigan et al. |
| 5,505,199 A | * 4/1996 | Kim ........................... 600/323 |
| 5,584,296 A | * 12/1996 | Cui et al. .................... 600/479 |
| 5,611,337 A | 3/1997 | Bukta |
| 5,638,818 A | 6/1997 | Diab et al. |
| 5,782,757 A | 7/1998 | Diab et al. |
| 5,817,010 A | * 10/1998 | Hibl ........................... 600/344 |
| 5,891,026 A | * 4/1999 | Wang et al. ................ 600/344 |
| 5,978,691 A | * 11/1999 | Mills .......................... 600/334 |
| 6,041,247 A | * 3/2000 | Weckstrom et al. ........ 600/323 |
| 6,088,607 A | 7/2000 | Diab et al. |
| 6,115,621 A | * 9/2000 | Chin .......................... 600/323 |

FOREIGN PATENT DOCUMENTS

| | | |
|---|---|---|
| CH | 682627 | 10/1993 |
| DE | 3516338 | 11/1986 |
| DE | 4423597 | 8/1995 |
| EP | 0267978 | 5/1988 |

OTHER PUBLICATIONS

"Nonivasive Assessment of Blood Gases, State of the Art", by J.S. Clark et al., Am. Rev. Resp. Dis. vol. 145, pp. 220–232.

"Biomedical Instrumentation and Technology", by Y. Mendelson and B. Yocum, vol. 25, 1991, pp. 472–480.

"Clinical Investigation of a New Combined Pulse Oximetry and Carbon Dioxide Tension Sensor in Adult Anesthesia", by Roman Rohling, MD & Peter Biro, MD DEAA, Journal of Clinical Monitoring and Computing, vol. 15, No. 1, Jan. 1999 pp23–27.

International Standard ISO 9919, International Organization for Standardization, Switzerland, 1992.

(List continued on next page.)

Primary Examiner—Eric F. Winakur
Assistant Examiner—Matthew Kremer
(74) Attorney, Agent, or Firm—Selitto, Behr & Kim

(57) ABSTRACT

A device for the combined measurement of the arterial oxygen saturation and the transcutaneous $CO_2$ partial pressure on an ear lobe comprises a sensor. The sensor has means for pulse oximetric measurement of the arterial oxygen saturation, means for measurement of the transcutaneous $CO_2$ partial pressure and means for warming a sensor contact surface intended for contact with the ear lobe. The device makes simple and reliable measurement of the arterial oxygen saturation and the transcutaneous $CO_2$ partial pressure possible on an ear lobe.

29 Claims, 3 Drawing Sheets

OTHER PUBLICATIONS

Sensor of Ullrich in detail (undated).
Prospectus of MicroGas 7650, Combi•M 82, Kontron Instruments, Apr. 1995 (4.95).
Kontron Instruments, MicroGas 7650 Combi•M 82 Sensor in detail (undated).
Huch et al., "Transcutaneous $PO_2$", Thieme–Stratton Inc., 1981, p. 88.
Prospectus "Der Kontinuierliche Überblick", Radiometer Copenhagen, 1993.
Two Prospectuses "TINA" radiometer, Radiometer Copenhagen (undated).
AARC Clinical Practice Guideline, Respiratory Care, Dec. 1991, vol. 36, No. 12.

Von H. Schubert, "Messtechnik in der Medizinischen Diagnostik", Medizintechnik, 2/94, pp. 66–68.

Huch, et al., "Patientenüberwachung durch transcutane $Pco_2$–Messung bei gleichzeitiger Kontrolle der relativen lokalen Perfusion", Anaesthesist 22, 1973, pp. 379–380.

Dr. R. Rohling, Affidavit relating to medical tests executed in Germany and Switzerland in 1997, Aug. 21, 2000.

Two sets of test result documentation from medical tests executed in Germany and Switzerland in 1997, by Dr. R. Rohling and Dr. R. Konrad, Summer 1997.

* cited by examiner

DEVICE FOR THE COMBINED MEASUREMENT OF THE ARTERIAL OXYGEN SATURATION AND THE TRANSCUTANEOUS $CO_2$ PARTIAL PRESSURE ON AN EAR LOBE

FIELD OF THE INVENTION

The invention relates to a device for the combined measurement of the arterial oxygen saturation and the transcutaneous carbon dioxide partial pressure on the ear.

BACKGROUND OF THE INVENTION

It is known to measure the oxygen saturation of the haemo-globin in arterial blood (arterial oxygen saturation) by means of a noninvasive optical method which is referred to as pulse oximetry. The principle of this method is based on measuring and evaluating changes in the absorption of light caused by the pulsatile inflow of arterial blood into a well-perfused part of the body (e.g. finger pad or ear lobe). The $SpO_2$ measured in this way normally provides reliable information about the patient's oxygenation. Pulse oximetry is routinely employed in various medical fields, in particular for intra- and postoperative patient monitoring.

However, information about oxygenation is not always sufficient on its own. It is frequently necessary also to know the arterial carbon dioxide partial pressure ($paCO_2$) in order to be able to assess the patient's respiratory functions. The methods currently available for measuring the $paCO_2$ are essentially the three described below:

1. Removal and analysis of an arterial blood sample. Although this method allows direct measurement of the $paCO_2$, it has the disadvantage that it is invasive and requires access to an artery. In addition, the measurement is not continuous and therefore does not allow changes in the $paCO_2$ to be monitored continuously. The method has the further disadvantage that the analytical result is usually available only after a delay of several minutes.

2. Capnometry. This is an optical absorption measurement in the infrared region used to determine the concentration of $CO_2$ in the expired gas mixture. The $paCO_2$ can be calculated from the $CO_2$ concentration in the end-expiratory phase. However, as indirect method, capnometry has the disadvantage that it does not always correctly reflect the $paCO_2$. Thus, it is known that this value is often an underestimate to varying extents. It is also possible for other parameters, e.g. a change in the cardiac output, to result in a change in the end-expiratory $CO_2$ concentration and thus cause an incorrect estimate of the $paCO_2$.

Furthermore, the possible applications of capnometry are restricted by the fact that it can be employed in general only for intubative, artificially ventilated patients. It is therefore in general impossible to determine the $paCO_2$ by capnometry during operations on nonventilated patients. Nor is capnometry suitable for monitoring the transition phase from artificial ventilation to spontaneous breathing. It is precisely during such a transition that continuous measurement of the $paCO_2$ is often required.

3. Transcutaneous $PCO_2$ measurement. This method is likewise indirect and makes use of the fact that carbon dioxide is able easily to diffuse through body tissue and skin. The gas is measured with a sensor attached to the surface of the skin. When a sensor of this type is warmed to a temperature of about 41° C. to about 45° C., this produces local dilatation and arterialization of the capillary bed at the measurement site. Under these conditions, the transcutaneous carbon dioxide partial pressure ($tcpCO_2$) measured there shows a good correlation with the arterial value. This makes it possible, with certain restrictions, to determine the $paCO_2$ with an accuracy which is sufficient for most applications.

Detailed information about the measurement methods mentioned and their clinical applications may be found, for example, in the review article "Noninvasive Assessment of Blood Gases, State of the Art" by J. S. Clark et al., Am. Rev. Resp. Dis., Vol. 145, 1992, pp. 220–232.

Of the abovementioned methods for $paCO_2$ measurement, at first sight the transcutaneous method appears to have the most advantages: this measurement is noninvasive, continuous and can also be employed for nonintubated patients. Nevertheless, transcutaneous $PCO_2$ measurement has not to date become widely used for intra- and postoperative patient monitoring. It is employed for this only extremely rarely, whereas it has long been established as a routine method in other medical fields, for example in intensive monitoring in neonatology.

One of the reasons for this is that the sensors currently available for $tcpCO_2$ measurement are suitable for application only to sites on the body to which access by the anaesthetist during an operation is usually difficult: a $tcpCO_2$ sensor must be applied by means of an adhesive ring which is adhesive on both sides to a well-perfused, hairless site of low convexity on the skin, with the diameter of the area of skin covered by the sensor and adhesive ring being about two to three centimetres. Particularly suitable measurement sites are therefore the thorax region, the abdominal regions and the inside of the upper arm or thigh. These sites are, however, not directly accessible for the anaesthetist, and can usually not be inspected either if they are covered. Thus, for example, it is difficult to check whether the sensor is adhering well or has become detached. Possible repositioning of the sensor during the operation is also difficult. In addition, on these sites on the body, the sensor may impede the surgeon or conflicts with the requirements for sterility in the vicinity of the operative field may occur. In addition to these difficulties which derive from the measurement site, application of a $tcpCO_2$ sensor is often regarded as complicated because a contact gel must be applied in order to avoid inclusions of air between sensor and skin. The dosage of this gel is critical because if the amount is too large the adhesion area of the adhesive ring would be wetted and, in this case, satisfactory attachment of the sensor would no longer be ensured. On the other hand, too small an amount of the gel would be ineffective.

There are no difficulties of this nature on application of a pulse oximeter sensor. This is usually attached by means of a clamp or an adhesive strip to a finger or an ear lobe. No special complexity is required for this. In contrast to a transcutaneous sensor, no contact gel is required. The measurement site on the ear is in particular usually easily accessible and easy to inspect by the anaesthetist. It is extremely rare for the surgeon to be impeded or problems to arise with the requirements for sterility there.

However, the disadvantage of pulse oximetric measurement on the ear lobe is that the signal measured there is often very weak. On the one hand, this derives from the fact that the thickness of the tissue from which the signal is obtained is relatively small by comparison with the finger pad. On the other hand, the ear lobe is often cold, as a result of the frequently low temperature in the operating theatre, and therefore poorly perfused. This may result in the signal measured on the ear being so weak that pulse oximetric measurement is no longer possible there. The anaesthetist is then forced to carry out the measurement on a finger. Although the finger is in principle also easily accessible as measurement site, its location is less favourable from the anaesthetist's point of view, who normally does his work near the patients head. An additional factor is that an arterial catheter or a cuff for measuring blood pressure is frequently attached to the patient's arm. Such an arm must not be used for pulse oximetric measurements because the latter would be impaired otherwise. The other arm is frequently less accessible, depending on the patient's position.

It may be stated in summary that the problems of monitoring the arterial oxygen saturation and the arterial $PCO_2$ in patients during and after surgical operations have by no means been satisfactorily solved yet.

The object of the present invention is therefore to provide a device which makes simple and reliable measurement of these two parameters possible on the measurement site preferred by the anaesthetist, the ear. It is additionally intended to ensure that a signal strength sufficiently high for pulse oximetric measurement is available.

SUMMARY OF THE INVENTION

This object is achieved according to the invention by a device for the combined measurement of the arterial oxygen saturation and the transcutaneous $CO_2$ partial pressure on an ear lobe, having a sensor which has means for pulse oximetric measurement of the arterial oxygen saturation, means for measuring the transcutaneous $CO_2$ partial pressure and means for warming a sensor contact surface intended for contact on the ear lobe.

For better understanding of the invention, firstly the two measurement processes will be described in somewhat more detail:

Pulse oximetric measurement makes use of the fact that the absorptivities of haemoglobin for light differ in its oxygen-saturated and its reduced forms. The absorption coefficient of blood for red light depends greatly on the oxygen content and is virtually independent thereof for light in the near infrared region. It is possible by measuring the ratio of the intensities of the light absorbed at the two wavelengths to determine the arterial oxygen saturation. The light sources normally used are two diodes (LED) which are located close together and have wavelengths of about 660 nm (red) and 890 nm (infrared). The light emitted by the LEDs is passed into a well-perfused part of the body and is there scattered and partly absorbed. The light emerging again from the part of the body is measured by a photodiode which is usually disposed opposite to the LEDs. The light measured by this photodiode at the two wavelengths consists of a stationary and a time-dependent component. The stationary component is essentially determined by absorption by bones, tissues, skin and non-pulsatile blood. The time-dependent component is caused by changes in absorption in the object of measurement elicited by the pulsatile flow of arterial blood. To determine the arterial oxygen saturation, the quotients of the pulse-modulated and the stationary components are formed separately for the two wavelengths. These quotients represent the primary signals measured. The $SpO_2$ is calculated from their amplitudes by means of an empirically determined function. The sensitivity of the pulse oximetric measurement is limited by the fact that interfering signals and electronic noise are superimposed on the signals measured. If the primary signals measured are too weak, reliable determination of the $SpO_2$ is no longer possible. The primary signals measured on the ear lobe are usually weaker by a factor of about 10 than the values measured on the finger, which is attributable mainly to the smaller thickness of tissue on the ear. It is easily possible with this signal strength which is low in any case, as mentioned above, for the pulse oximetric measurement on the ear lobe no longer to be possible if it is very poorly perfused.

Transcutaneous $pCO_2$ measurement is based on an electrochemical principle. The measurement takes place potentiometri-cally by determining the pH of a thin layer of an electrolyte solution which is coupled to the skin via a hydrophobic membrane which is very gas-permeable. A change in the $pCO_2$ on the surface of the skin causes a change in pH of the electrolyte solution, which is proportional to the logarithm of the $pCO_2$ change. The pH is determined, for example, by measuring the potential between a miniature glass pH electrode and an Ag/AgCl reference electrode. The $tcpCO_2$ sensor contains a heating element which heats it to a temperature of about 41° C. to 45° C. As mentioned at the outset, this produces local dilatation and arterialization of the capillary bed at the measurement site, which causes the $tcpCO_2$ measured there to correlate well with the arterial value.

The essential feature of the invention described hereinafter is that the two measurement functions for $SpO_2$ and $tcpCO_2$ are integrated into one unit so that simultaneous measurement thereof on the ear lobe is possible with an accuracy and reliability which is sufficient for clinical requirements. An important component of this unit is, besides the actual measuring part, the appliance for attaching the sensor to the ear.

The fact that such a combined sensor has not previously been disclosed, despite the evident clinical demand, is attributable to various reasons:

On the one hand, the necessary miniaturization, especially of the $tcpCO_2$ measuring part, involves considerable design difficulties which, however, will not be dealt with in detail because the invention does not relate to the solutions used therefor. On the other hand, it was not to be expected directly that the two very different measurement functions can be combined in a miniaturized unit in such a way that they do not have adverse effects on one another and that no other disadvantageous effects occur either. Thus, for example, there were doubts about whether the potential of the Ag/AgCl reference electrode could be influenced by the light used for the $SpO_2$ measurement, as a result of a photochemical reaction. However, no such influence has been detectable.

On the other hand, another concern proved to be justified: it was suspected that some of the components required for the $tcpCO_2$ measurement would cause an optical shunt which might impair the $SpO_2$ measurement. This proved to be correct and resulted, in a preferred embodiment, in specific design measures which will be dealt with in detail hereinafter.

Apart from these purely technical doubts, it was unknown whether the ear lobe would in fact be suitable, for physiological reasons, for transcutaneous measurement of the $pCO_{21}$ that is to say whether measurement there is possible with adequate accuracy and a sufficiently short reaction time (in vivo response time) to changes in the arterial $pCO_2$. Thus, for example, transcutaneous measurement on the finger pad cannot, although it is also well perfused, be used for clinical application because the in vivo response time there is too long. Nor was it directly evident whether a reliable and sufficiently stable attachment of the sensor to the ear lobe is possible without impeding perfusion in the capillary tissue near the surface on the measurement site. Even slight application of pressure (for example by the force of the spring of an earclip) may cause such an impediment. Although this would be relatively uncritical for pulse oximetric measurement, emptying of the blood capillaries near the surface may cause considerable problems for the transcutaneous measurement: these comprise, on the one hand, the fact that the carbon dioxide gas diffuses to the surface of the skin from relatively deep-lying capillaries and thus the diffusion pathway is extended. This may lead to falsification of the measured result and a prolongation of the in vivo response time. On the other hand, in the extreme case, the absence of perfusion near the surface may also lead to burn injuries if the heat supplied by the sensor is not removed quickly enough. This is a danger especially with high sensor temperatures of 44° C. and 45° C., which are close to the critical value for protein decomposition to start. The provision of a suitable appliance for attaching the sensor to the ear is therefore an important and integral component of the invention.

A preferred example of the sensor and two examples of appliances for attachment to the ear lobe are described hereinafter with reference to the appended drawings.

DETAILED DESCRIPTION OF THE DRAWINGS

Figures 1A, 1C:
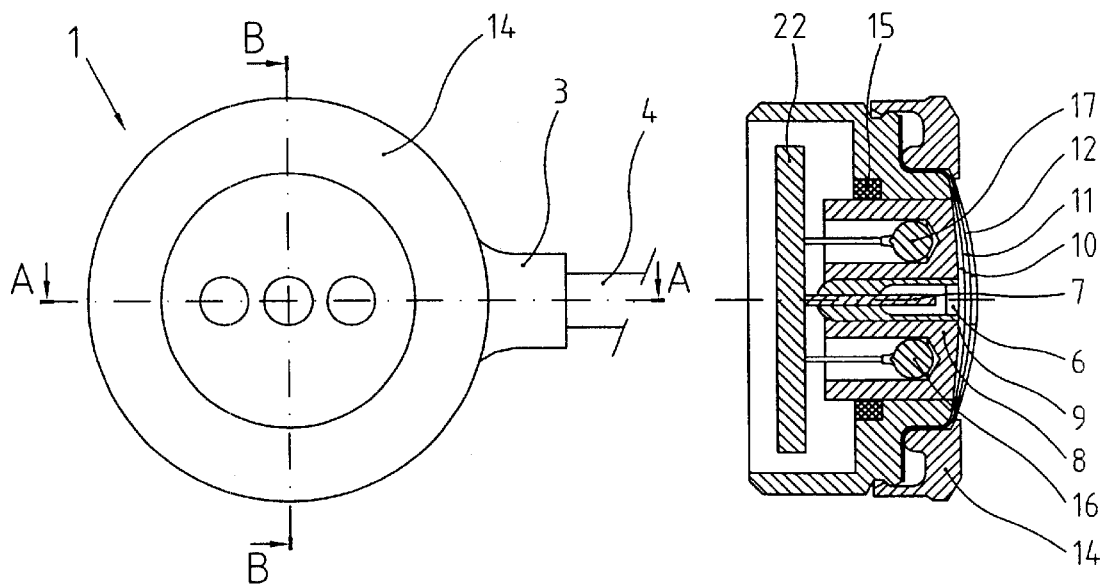
FIG. 1A shows a schematic top view of a combined sensor according to the invention for pulse oximetric $SpO_2$ measurement and transcutaneous $tcpCO_2$ measurement.
FIG. 1C shows a sectional view of the sensor along the line B—B in FIG. 1A.
Figures 1B, 1D:
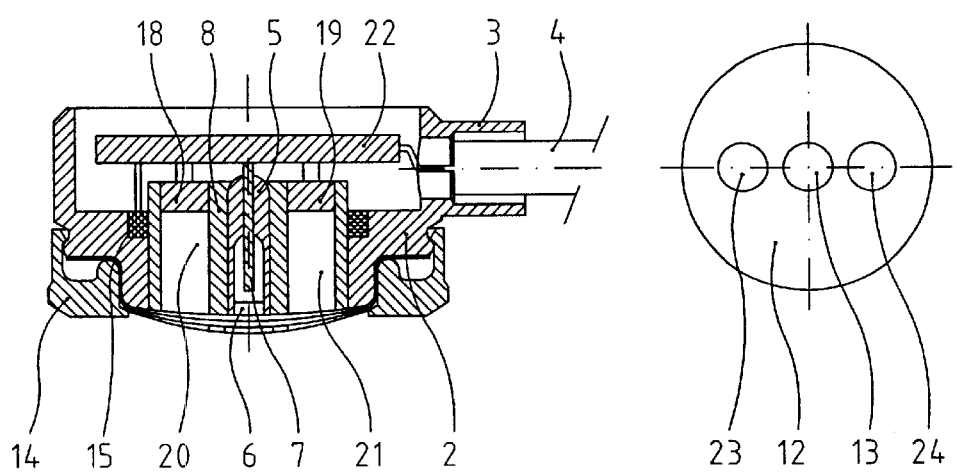
FIG. 1B shows a sectional view of the sensor along the line A—A in FIG. 1A.
FIG. 1D shows a top view of the sensor contact surface intended to make contact on an ear lobe.

FIG. 1A shows a top view of a sensor 1 in which the section surfaces of the cross-sectional views in FIGS. 1B (A—A) and 1C (B—B) are indicated. The sensor head consists of a circular plastic housing 2 with a neck-like attachment 3 through which the connecting cables 4 to the measuring apparatus are led out. The housing contains both the components required for the measurement functions and various electronic components as described hereinafter.

A glass pH electrode 5 is located in the central axis of the sensor. It comprises a cylindrical glass stem onto whose front end a pH-sensitive glass layer 6 is fused. An internal reference electrode with a platinum lead wire 7 fused into the glass is located inside the glass cylinder. The pH electrode 5 is embedded in a silver block 8 whose surface is covered with a chloride layer 9. The surface of the silver block thus forms an Ag/AgCl electrode which acts as reference electrode for the pH measurement. An electrolyte solution whose pH will be measured is located in a porous hydrophilic spacer 10 which is covered with a gas-permeable hydrophobic membrane 11 (for example Teflon®). To protect the membrane from mechanical damage, it is covered with a metal diaphragm 12. This diaphragm has in the centre (above the pH-sensitive glass layer 6) an aperture 13 through which the carbon dioxide gas to be measured is able to diffuse into the electrolyte solution at the site of the pH-sensitive glass layer. The spacer 10, the membrane 11 and the metal diaphragm 12 are attached to the sensor housing 2 by means of a clamping ring 14. The silver block 8 additionally has the function of a heating element. A heating wire 15 is coiled around it and heats it to the temperature of 41° C. to 45° C. required for the transcutaneous measurement. As is evident from FIG. 1C, two thermistors 16 and 17 are embedded in two holes drilled in the silver block. These thermistors are used to control and monitor the chosen sensor temperature. The optical components required for the pulse oximetric measurement are evident in the cross section in FIG. 1B. These are two LEDs 18 which are attached closely together on a ceramic support, and a photodiode 19. The light from and to these components is passed through two cylindrical light channels 20 and 21 which consists of two holes drilled in the silver block and filled with light-transmitting material. All the electrical connections from and to the various components are passed to an electronic unit 22 in which some of the signal processing is undertaken. The connecting cables to the measuring apparatus originate from this electronic unit and are passed to the outside through the sensor neck 3, as mentioned.

FIG. 1D, finally, shows a top view of the metal diaphragm 12 which forms the actual contact surface of the sensor. As already mentioned, there is in the middle of the diaphragm a perforation 13 through which the carbon dioxide gas is able to reach the electrolyte on the pH electrode. The two perforations 23 and 24 which are arranged peripheral thereto serve to allow the light emitted by the LEDs and scattered back from the tissue to pass through. The metal diaphragm has a light-reflecting surface on the side facing the ear lobe.

Figures 2A, 2B:
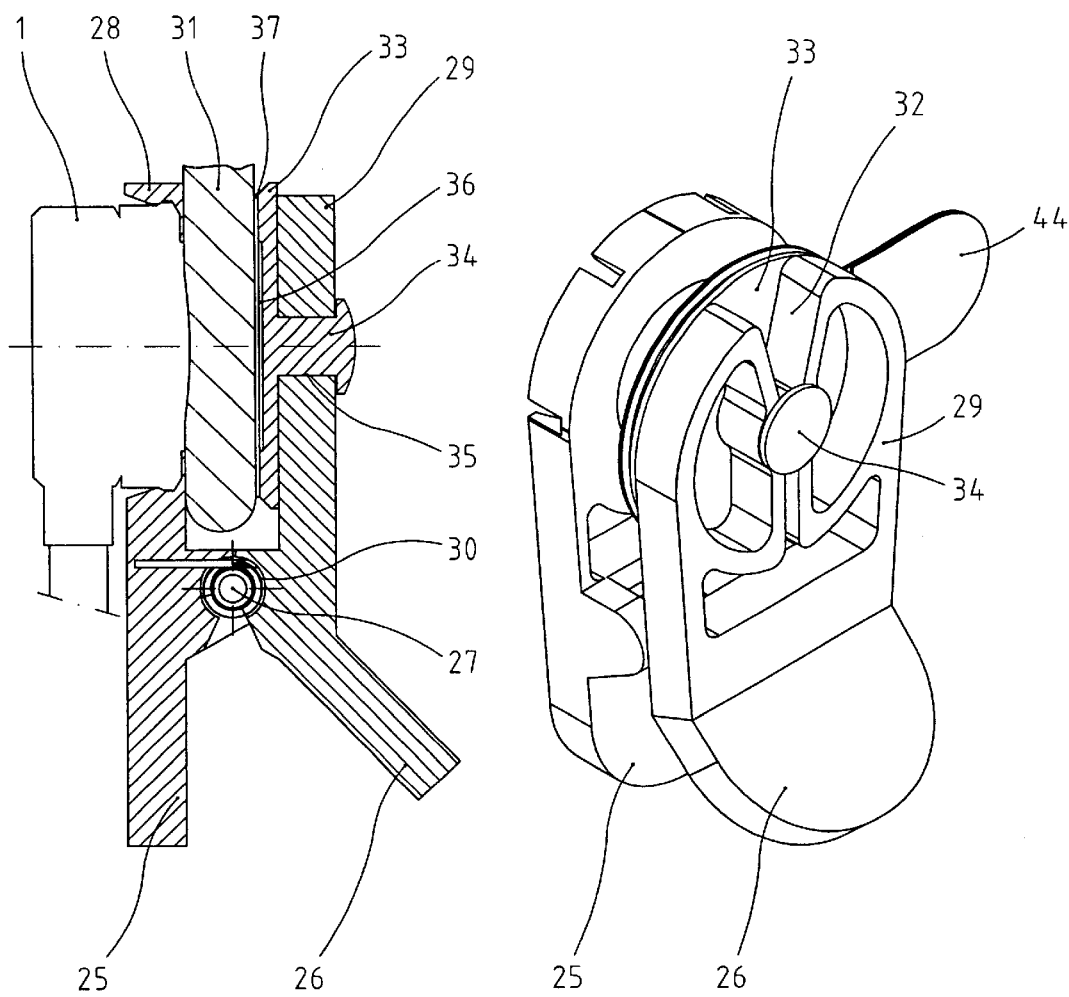
FIG. 2A shows a device for combined measurement of the arterial oxygen saturation and the transcutaneous $CO_2$ partial pressure according to the invention attached to an ear lobe by means of a clip in partial sectional view.
FIG. 2B shows a perspective view of the device of FIG. 2A.

FIG. 2A depicts a clip for attaching the sensor to an ear lobe 31 in cross section. This comprises two clip halves 25 and 26 which are connected together by a hinge pin 27. The two clip halves each form a gripping jaw 28 and 29, and these are pretensioned slightly relative to one another by a spring 30. In the middle of the gripping jaw 28 there is an aperture through which the sensor 1 is introduced far enough for it to make contact with the skin of the ear lobe 31 and snap into the gripping jaw 28. The opposite gripping jaw 29 is designed, as can be seen in FIG. 2B, so that a stud 34 which is attached to the rear side of a fastening disc 33 can be introduced through a slit-like aperture 32 therein. The stud 34 serves to retain the fastening disc 33 in a circular cutout 35 provided therefor in the gripping jaw. For manipulation of the fastening disc 33, a holding plate 44 is attached thereto. On the front side of the fastening disc facing the sensor there is a light-reflecting metal foil 36. A transparent adhesive sheet 37 which is adhesive on both sides is applied on top of the latter. The retention of the complete device (sensor and clip) on the ear lobe 31 is achieved primarily by the action of the adhesive sheet 37, which has adequate adhesive strength. The tension spring 30 merely serves to bring the sensor into contact with the skin surface with minimal pressure. The sensor can be temporarily removed, if necessary, from the gripping jaw 28 without the need to detach the clip from the ear. It is additionally possible to rotate the sensor around its axis so that the sensor cable can be optimally positioned.

Figures 3A, 3B:
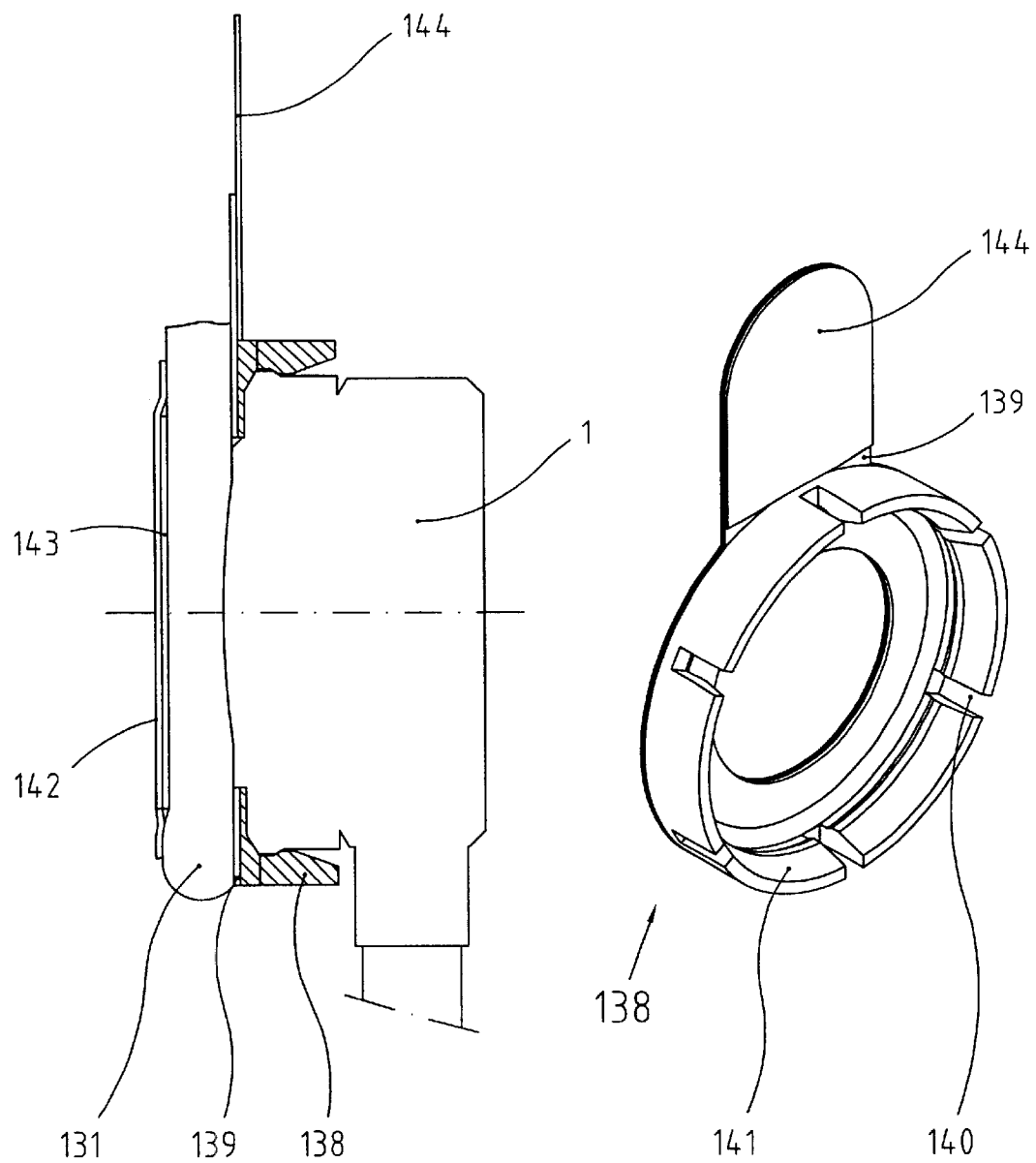
FIG. 3A shows a device for combined measurement of the arterial oxygen saturation and the transcutaneous $CO_2$ partial pressure according to the invention attached by means of an annular retainer to an ear lobe in partial sectional view.
FIG. 3B shows a perspective view of the annular retainer of the device of FIG. 3A.

FIG. 3A shows another example of an attachment appliance which consists essentially of an annular retainer 138 into which the sensor 1 is introduced until it makes contact with the skin of the ear lobe 31. An adhesive sheet 139 which is adhesive on both sides is applied to the surface of this retainer facing the ear and has sufficient adhesive strength to attach the sensor stably to the ear lobe. As is evident from the perspective depiction of the annular retainer 138 in FIG. 3B, several slits 140 are arranged in the outer wall of the retainer and divide the wall into individual elastic segments 141. This makes it possible to snap the sensor straightforwardly into the retainer and remove it again too. It is thus possible to remove the sensor, if necessary, temporarily from the retainer without the need to detach the latter from the ear. It is possible in this case too for the sensor to be rotated around its axis so that the sensor cable can be optimally positioned. To manipulate the annular retainer 138, a holding plate 144 is additionally bonded to the adhesive sheet 139. On the side of the ear lobe opposite to the sensor, a light-reflecting metal foil 143 is attached by means of an adhesive strip 142.

It is self-evident that the embodiments described above can be modified by known, analogous arrangements without this altering the basic idea and the scope of the invention. In particular, it is possible to use, instead of a glass electrode 5 for measuring the pH, any other suitable pH measuring device such as, for example, an electrode based on metal oxides (for example iridium/iridium oxide). It is also possible to use instead of a light-reflecting metal foil 36 or 143 a metallized, light-reflecting plastic sheet or a white, light-reflecting sheet. Also suitable instead of the coiled heating wire 15 are other, miniaturizable heating elements such as, for example, thick film heating resistances or NTC resistances.

The sensor according to the invention with the relevant attachment appliances has a number of advantages, which are explained below:

The obviously most important advantage is that measurement of the two parameters $SpO_2$ and $tcpCO_2$ is simplified by the fact that only one sensor is required therefor and that this sensor can be applied to a site which is readily accessible to the anaesthetist.

Another advantage is that the heating of the measurement site improves the pulse oximetric measurement. The heating causes increased perfusion not only in capillaries near the surface, which is necessary for the transcutaneous measurement, but also in the entire ear lobe. This makes it possible to obtain a sufficiently strong pulse oximetric signal for a longer period. It is true that it is known to heat a pulse oximetric sensor in order to increase local perfusion and thus obtain a stronger measured signal (Y. Mendelson, B. Yocum in "Biomedical Instrumentation and Technology", Vol. 25, 1991, pp. 472–480). However, no use of this has been made hitherto in commercial embodiments of pulse oximeters. This is attributable primarily to reasons of cost because incorporation of the heating element and of the temperature sensor would multiply the cost of the production of the sensor. An additional factor is that the control of the heating temperature in the measuring apparatus requires relatively great complexity in particular because of the strict requirements for reliability and accuracy. This cost argument does not apply to the combined sensor according to the invention because the heating of the sensor is necessary for the transcutaneous measurement in any case and thus does not cause an increase in the cost of the pulse oximetric measurement part.

An additional increase in the signal strength is achieved by a special design measure: in contrast to conventional ear sensor devices in which the light-emitting LEDs and the photodiode are attached to opposite gripping jaws of the sensor device, in the case of the measuring device according to the invention these components are preferably located on the same side. The light emitted by the LEDs passes through the ear lobe and reaches the opposite reflecting sheet of the attachment appliance and is reflected back there. Since the metal diaphragm of the sensor likewise consists of a reflecting material, multiple reflections are also possible. The light which finally reaches the photodiode thus derives from a considerably larger region of tissue than in the case of conventional ear sensors. The additional increase in the sensitivity of the pulse oximetric measurement resulting from this is a further important advantage of the invention.

There were initially doubts about the idea of arranging the LEDs and the photodiode side by side and not opposite. As mentioned above, it was suspected that an optical shunt between the LEDs and the photodiode might occur, i.e. part of the light emitted by the LEDs might reach the photodiode directly without previously entering the tissue of the ear lobe. This would artificially increase the intensity of the stationary component of the light reaching the photodiode, which would falsify the measured result. A conceivable route for such a shunt in the embodiment of the sensor described herein is, in particular, the space between the silver block and the metal diaphragm. This space is filled by the spacer and the gas-permeable membrane, both of which are light-transmitting. In order to minimize the proportion of the light routed via this shunt, it proved to be expedient to arrange the LEDs and the photodiode not, as otherwise usual, close to the surface but in the interior of the sensor. The concentration of the emerging light through the light channel results in the proportion of light scattered into the shunt region being extremely small. This is also a beneficial effect from the fact that the silver surface is covered with a black, nonreflective silver chloride layer. The effect of the shunt on the accuracy of measurement proved to be negligible.

A further advantage of the sensor according to the invention is that the use of contact gel is not absolutely necessary for the transcutaneous $pCO_2$ measurement. This has surprisingly emerged from test measurements to date. The exact reasons for this are not yet known, but it may be assumed that it is connected with the characteristics of the skin of the ear lobe. Compared with other sites on the skin where the transcutaneous $pCO_2$ measurement is normally carried out, the skin is smoother and has fewer pores at which air is able to remain entrapped. The fact that no contact gel is required leads to a considerable simplification of the measurement complexity because application of the gel is often felt to be tiresome for the reasons described at the outset.

What is claimed is:

1. A device for a combined measurement of arterial oxygen saturation and transcutaneous $CO_2$ partial pressure on an ear lobe, comprising a sensor which has means for pulse oximetric measurement of the arterial oxygen saturation; means for measurement of the transcutaneous $CO_2$ partial pressure; and means for warming a sensor contact surface intended for contact with the ear lobe; said device further comprising means for attaching said device to an ear lobe such that said device is in contact with the ear lobe with a minimal pressure on the ear lobe for minimizing interference with the pulse oximetric measurement of the arterial oxygen saturation and the transcutaneous $CO_2$ partial pressure, said sensor being rotatably attached to said means for attaching said device to an ear lobe, said means for pulse oximetric measurement of the arterial oxygen saturation including at least two LEDs and one photodiode which are arranged so that when the device is attached to an ear lobe they are located on the same side of the ear lobe, and which are arranged in depressions forming light channels and point towards the sensor contact surface.

2. Device according to claim 1, in which the light channels are cylindrcal holes.

3. Device according to claim 1 or 2 having a light-reflecting surface which is arranged so that when the device is attached to the ear lobe, the light-reflecting surface is located on the opposite side of the ear lobe relative to the LEDs and the photodiode.

4. Device according to claim 1 or 2, in which the light channels are arranged in a silver block.

5. Device according to claim 4, in which the means for warming the sensor contact surface comprise means for warming the silver block.

6. Device according to claim 1 or 2, in which the means for measurement of the transcutaneous $CO_2$ partial pressure comprise an Ag/AgCl electrode and a glass pH electrode.

7. Device according to claim 1 or 2, in which the means for measurement of the transcutaneous $CO_2$ partial pressure comprise an Ag/AgCl electrode and a metal oxide electrode.

8. Device according to claim 1 or 2, in which a sensor contact surface is formed by a reflecting diaphragm which has perforations.

9. Device according to claim 8, in which at least two of the perforations are arranged in front of the means for the pulse oximetric measurement of the arterial oxygen saturation.

10. Device according to claim 8, in which at least one of the perforations is arranged in front of the means for measurement of the transcutaneous $CO_2$ partial pressure.

11. Device according to claim 1 or 2, having a thermistor to control the temperature on the sensor contact surface.

12. Device according to claim 11 having an additional thermistor to monitor the temperature on the sensor contact surface.

13. Device according to claim 1 or 2, wherein said means for attaching said device to an ear lobe has a clip with a first gripping jaw and a second gripping jaw, with the sensor being attached to the first gripping jaw.

14. Device according to claim 13, in which the sensor on the first gripping jaw is removable.

15. Device according to claim 13, in which an adhesive sheet is attached to the second gripping jaw for making the device adhere to an ear lobe, and the first and the second gripping jaws are pretensioned relative to one another so that when the device is attached to an ear lobe the first gripping jaw is in contact with the ear lobe and exerts a pressure on the earlobe such a that the pulse oximetric measurement of the arterial oxygen saturation and the measurement of the transcutaneous $pCO_2$ partial pressure are negligibly impaired.

16. Device according to claim 15, in which when the device is attached to an ear lobe the contact pressure of the first gripping jaw on the ear lobe is less than 2500 N/m².

17. Device according to claim 1 or 2, wherein said means for attaching said device to an ear lobe has a retainer to which said sensor is removably attached, said retainer being provided with an a first adhesive sheet to make it adhere to the ear lobe.

18. Device according to claim 17, in which a light-reflecting surface is provided with an adhesive sheet for making it adhere to the side of the ear lobe opposite to the sensor.

19. A device for combined measurement of arterial oxygen saturation and transcutaneous $CO_2$ partial pressure on an ear lobe, comprising a sensor which has means for pulse oximetric measurement of the arterial oxygen saturation; means for measurement of the transcutaneous $CO_2$ partial pressure; and means for warming a sensor contact surface intended for contact with the ear lobe, said device further comprising means for attaching said device to an ear lobe such that said device is in contact with the ear lobe with a minimal pressure on the ear lobe for minimizing interference with the pulse oximetric measurement of the arterial oxygen saturation and measurement of the transcutaneous $CO_2$ partial pressure, said sensor being rotatably attached to said means for attaching said device to an ear lobe.

20. Device according to claim 19, wherein said means for attaching said device to an ear lobe is a clip with a first gripping jaw and a second gripping jaw, with the sensor being attached to the first gripping jaws.

21. Device according to claim 20, in which the sensor on the first gripping jaw is removable.

22. Device according to claim 20, in which an adhesive sheet is attached to the second gripping jaw for making the deviceadhere to the ear lobe.

23. Device according to claim 19, in which when the device is attached to the ear lobe the contact pressure of the first gripping jaw on the ear lobe is less than 2500 N/m².

24. Device according to claim 19, in which the sensor is removably and rotatably attached in a retainer which is provided with an adhesive sheet to make it adhere to an ear lobe.

25. A method for measuring arterial oxygen saturation and trancutaneous $CO_2$ partial pressure on an ear lobe, comprising the steps of attaching, to an ear lobe, a device comprising means for attaching said device to the ear lobe and a sensor having means for pulse oximetric measurement of the arterial oxygen saturation, means for measurement of the transcutaneous $CO_2$ partial pressure, and a contact surface for contacting the ear lobe, said sensor being rotatable attached to said means for attaching said device to the ear lobe, so that said contact surface of the sensor contacts the ear lobe so as to minimize interference with the pulse oximetric measurement of the arterial oxygen saturation and the measurement of the transcutaneous $CO_2$ partial pressure;

warming said contact surface to a temperature such as produces dilation and arterialization of the ear lobe in proximity to said contact surface, and measuring said arterial oxygen saturation; and measuring said transcutaneous $CO_2$ partial pressure, wherein the steps of measuring said arterial oxygen saturation and measureing said transcutaneous $CO_2$ partial pressure are performed concurrently with one another.

26. The method of claim 25, wherein said contact surface exerts at the a minimal pressure on the ear lobe while in contact with said ear lobe.

27. The method of claim 26, wherein said at a minimal pressure is less than 2500 N/m².

28. The method of claim 25, wherein said sensor comprises a means for warming said contact surface during said warming step.

29. The method of claim 25, wherein said temperature is in the,range of about 41° C. to about 45° C.

* * * * *